United States Patent [19]

Dittrich

[11] Patent Number: 4,844,053

[45] Date of Patent: Jul. 4, 1989

[54] FLEXIBLE TUBULAR DEVICE

[75] Inventor: Horst Dittrich, Immendingen, Fed. Rep. of Germany

[73] Assignee: Karl Storz GmbH & Co., Fed. Rep. of Germany

[21] Appl. No.: 187,425

[22] Filed: Apr. 28, 1988

[30] Foreign Application Priority Data

Apr. 28, 1987 [DE] Fed. Rep. of Germany ....... 3714141

[51] Int. Cl.$^4$ .................................................. A61B 1/00

[52] U.S. Cl. .......................................... 128/4; 138/120

[58] Field of Search ........................ 128/4, 6; 138/120

[56] References Cited

U.S. PATENT DOCUMENTS

| | | | |
|---|---|---|---|
| 3,091,235 | 5/1963 | Richards | 128/6 |
| 3,583,393 | 6/1971 | Takahashi | 128/4 |
| 4,328,839 | 5/1982 | Lyons et al. | 138/120 |

*Primary Examiner*—William H. Grieb

*Attorney, Agent, or Firm*—Barnes & Thornburg

[57] ABSTRACT

A flexible tubular device composed of a plurality of movably interconnected tubular elements is provided, particularly for use as a protective tube for a flexible endoscope. At least two first extensions are provided at one end of each tubular element. Each of the extensions engages into a corresponding recess of an adjacent tubular element. The ends of the first extensions are bifurcated for locking the first extensions in the recesses.

4 Claims, 1 Drawing Sheet

FLEXIBLE TUBULAR DEVICE

BACKGROUND AND SUMMARY OF THE INVENTION

The present invention relates to a flexible tubular device comprising a plurality of movably interconnected tubular elements.

Flexible tubular devices having a plurality of tubular elements can be used in applications such as those of flexible endoscopes. In these and other applications, it is particularly important that the open internal diameter of the individual tubular elements not be excessively restricted. The open internal diameter can accommodate inserts such as the optical conductor of a flexible endoscope. For interconnecting the individual tubular elements in known flexible tubular devices, the individual tubular elements have been provided with projections by which they are connected to an adjacent element. Screws or rivets passing through openings in the projections have been used as fastener elements.

A number of disadvantages are associated with these known interconnecting arrangements. The screws or rivets used as fasteners create a comparatively considerable restriction of the diameter available for inserts. Moreover, the provision of additional rivets is hardly possible, specifically in elements which are to be used in flexible endoscopes and have a diameter in the range of 3 to 5 mm, for instance.

An object of the present invention is to provide a flexible tubular device composed of a plurality of movably interconnected tubular elements, wherein the connecting of the individual tubular elements creates only a minimal restriction of the free diameter available.

This object is achieved by providing tubular elements each having an end with at least two first extensions. Each of the extensions engages into a corresponding recess of an adjacent tubular element. In order to prevent a movement of the extensions out of the recesses, the ends of the extensions are bifurcated. This arrangement allows for a reliable flexible interconnection of the individual tubular elements without an excessive restriction of the free tube diameter. Moreover, the flexible tubular device is simple and inexpensive to produce from prefabricated tube elements.

According to advantageous features of certain preferred embodiments of the invention, the bifurcated ends of the extensions are split and bent in the direction of the tube axis. Splitting in this direction is not only easy to perform, but also allows for a reliable connection which does not impair the flexibility of the element.

According to other advantageous features of certain preferred embodiments of the invention, the extensions are initially bent in a direction almost normal to the tube axis. Following this first section, is an adjacent second section which extends approximately parallel to the tube axis, and an additional third section which extends normal to the tube axis, and extends through a recess of an adjacent tubular element. Extending from this additional third section, is a final section which includes an end which is bifurcated and spread apart in the direction of the tube axis after insertion through the recess.

In terms of production engineering, these embodiments are uncomplicated while allowing a limit of the minimum radius of curvature of the flexible tubular device. This feature is even more improved in certain preferred embodiments which include a set of second extensions on an end opposite the first extensions, and the recesses are disposed in the set of second extensions.

According to other advantageous features of certain preferred embodiments of the invention, the second section adjacent the bent section, which is approximately parallel to the tube axis, is offset inwardly from the interior wall of the tubular elements. Thus, the third section extends from the interior of the tube through the recess, and the fourth section including the bifurcated end is on the exterior of the tube. This arrangement provides a largely smooth outside surface of the flexible tubular device.

Other objects, advantages and novel features of the present invention will become apparent from the following detailed description of the invention when considered in conjunction with the accompanying drawings.

DETAILED DESCRIPTION OF THE DRAWINGS

Figure 1:
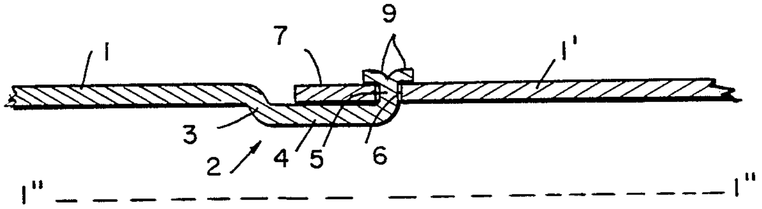
FIG. 1 is a cross-sectional view through one portion of the tubular elements according to certain preferred embodiments of the present invention.
Figure 2:
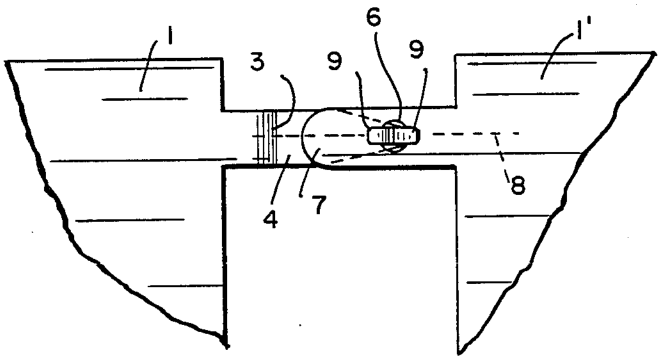
FIG. 2 is a plan view of the elements shown in FIG. 1.

The drawings illustrate two tubular elements 1 and 1′. It is contemplated that a plurality of tubular elements form the flexible tubular device.

The tubular element 1 includes two extensions 2 of which only one is shown in the drawing. Each of the extensions 2 is provided with an inwardly bent section 3, a section 4 extending parallel to a tube axis 1″, and a section 5 extending normal to the tube axis 1″.

The section 5 passes through a recess 6 which is located in an extension 7 of the adjacent tubular element 1′. The ends 9 of the section 5 are split in the direction of the tube axis 1″ along a line 8, and are bent in forward or rearward direction in the orientation of the tube axis. This arrangement prevents the section 5 from withdrawing from the recess 6.

However, it is also ensured that the elements have the required flexibility. Splitting and bending of the section 5 at end 9 is easily accomplished. In addition, the bent extension requires little space, and reduces the free diameter only slightly. It is contemplated that the free diameter be used for an endoscope. The reduction of the free diameter does not exceed the volume claimed, for instance, by openings, cutouts, etc. which are provided in the tube wall for attachment of insert elements such as cables.

Even though the invention has been described in the foregoing with reference to a particular embodiment, the description does not limit the general inventive idea of the present invention in any way.

For example, it is also contemplated to provide even more than two extensions whose terminal parts are engaged into corresponding recesses in an adjacent tubular element.

Although the present invention has been described and illustrated in detail, it is to be clearly understood that the same is by way of illustration and example only, and is not to be taken by way of limitation. The spirit and scope of the present invention are to be limited only by the terms of the appended claims.

What is claimed:

1. Flexible tubular apparatus particularly a protective tube for a flexible endscope comprising:

a plurality of movably interconnected tubular elements, each of said tubular elements including at least two first extensions extending from a first end and at least two corresponding recesses on a second end, said at least two first extensions of each of said tubular elements engaging in said corresponding recesses of an adjacent tubular element thereby interconnecting adjacent tubular elements, each of said at least two first extensions including bifurcated ends for locking said extensions into said recesses, wherein said adjacent tubular elements are arranged about a common tube axis, said bifurcated ends including ends split and spread along a line approximately parallel to said tube axis.

2. Flexible tubular apparatus particularly a protective tube for a flexible endscope comprising:

a plurality of movably interconnected tubular elements, each of said tubular elements including at least two first extensions extending from a first end and at least two corresponding recesses on a second end, said at least two first extensions of each of said tubular elements engaging in said corresponding recesses of an adjacent tubular element thereby interconnecting adjacent tubular elements, each of said at least two first extensions including bifurcated ends for locking said extensions into said recesses, wherein said at least two first extension include:

a first section bent approximately transverse to said tube axis;

a second section extending from said first section approximately parallel to said tube axis;

a third section extending from said second section approximately transverse to said tube axis an leading through said adjacent tubular element corresponding recess on a first side of said recess; and a fourth section including said bifurcated extension end, said bifurcated extension end including ends split and spread along a line approximately parallel to said tube axis on a second side of said adjacent tubular element corresponding recess, opposite said first side.

3. Apparatus as in claim 2, wherein said second section is offset inwardly from an interior wall of said tubular elements.

4. Flexible tubular apparatus particularly a protective tube for a flexible endscope comprising:

a plurality of movably interconnected tubular elements, each of said tubular elements including at least two first extensions extending from a first end and at least two corresponding recesses on a second end, said at least two first extensions of each of said tubular elements engaging in said corresponding recesses of an adjacent tubular element thereby interconnecting adjacent tubular elements, each of said at least two first extensions including bifurcated ends for locking said extensions into said recesses, wherein each of said tubular elements includes at least two second extensions on an end opposite said at least two first extensions, said recesses being disposed in said at least two second extensions.

* * * * *